United States Patent [19]
Beachey

[11] 4,284,537
[45] Aug. 18, 1981

[54] CONJUGATE OF STREPTOCOCCAL M PROTEIN PEPTIDE VACCINE

[75] Inventor: Edwin H. Beachey, Memphis, Tenn.

[73] Assignee: The United States of America as represented by the Department of Health and Human Services, Washington, D.C.

[21] Appl. No.: 165,619

[22] Filed: Jul. 3, 1980

[51] Int. Cl.³ .................. A61K 39/07; A61K 39/385; A61K 39/40; A61K 39/44
[52] U.S. Cl. .......................................... 260/6; 424/85; 424/87; 424/88; 424/92
[58] Field of Search ................. 260/6; 424/85, 87, 88, 424/92

[56] References Cited

U.S. PATENT DOCUMENTS 3,963,691  6/1976  Hoffman et al. ................. 260/112 R

OTHER PUBLICATIONS

Hosp. Practice, 14: 49–57, Nov. 1979, Brachey et al.

Primary Examiner—Howard E. Schain
Attorney, Agent, or Firm—John S. Roberts, Jr.

[57] ABSTRACT

Certain peptide fragments of streptococcal M protein named CB6 and CB7 have been linked to a protein carrier which is polylysine. The conjugate has proved immunogenic in rabbits producing protective antibodies against the whole group A streptococcus.

6 Claims, No Drawings

CONJUGATE OF STREPTOCOCCAL M PROTEIN PEPTIDE VACCINE

It was known recently in the art to prepare a vaccine known as the streptococcal M protein vaccine which is described by chemical and physical parameters below.

In the present development, this vaccine has been purified, achieving a peptide fragment of streptococcal M protein and the complete amino acid sequence to this fragment has been determined and is listed below.

More important, this fragment has now been linked to a protein carrier, which is a polylysine molecule and the conjugate has proved immunogenic in animals, such as rabbits, producing protective antibodies against the whole group A streptococcus. In other words, a peptide fragment of streptococcal M protein has been purified and its complete amino acid sequence has been determined.

The present inventors have been able to covalently link this fragment to a carrier polylysine molecule and show that it raises protective antibodies in rabbits against the whole group A streptococci. The process of producing the conjugate consists of reacting either CB6, CB7 or both with polylysine. A specific example of the process is set out post in Example 3.

The main desired use of the peptide vaccine is to prevent acute rheumatic fever which is triggered by group A streptococcal infections. There is also the additional possibility that group A streptococci may develop antibiotic resistance sometime in the future, in which case the present pep M vaccines would have greater and wider application.

PRIOR ART STATEMENT

Beachey et al, "A Strep Vaccine: How Close?" *Hosp. Pract.*, 14:49–57, November 1979.

Beachey et al, "Primary Structure of Protective Antigens of Type 24 Streptococcal M Protein," *J. Biol. Chem.*, 1980 (in press).

THE INVENTION

The complete amino acid sequence of two cyanogen bromide peptide fragments (CB6 and CB7) of type 24 streptococcal M protein purified from a peptic extract of the organism was determined by automated Edman degradation of the uncleaved peptides and their tryptic peptides. The sequence of CB6 was found to be Asn-Phe-Ser-Thr-Ala-Asp-Ser-Ala-Lys-Ile-Lys-Thr-Leu-Glu-Ala-Glu-Lys-Ala-Ala-Leu-Glu-Ala-Arg-Gln-Ala-Glu-Leu-Glu-Lys-Ala-Leu-Glu-Gly-Ala-Hse. The sequence of CB7 was identical except for substitutions of Ala, Lys and Asp at positions 21, 24 and 26, respectively. The protective immunogenic properties of these peptide fragments were studied in rabbits. Although neither peptide is immunogenic alone, when covalently conjugated with a polylysine carrier, both become highly immunogenic, producing type specific opsonic and bactericidal antibody responses against the type 24 vaccine strain of *Streptococcus pyogenes*.

The active fragments CB6 and CB7 have been conjugated with polylysine utilizing carbodiimide; see Williams and Chase, *Methods of Immunology and Immunochemistry*, Vol. I, 1967, pages 155–156.

These present studies show the complete covalent structure of a polypeptide antigen which encompasses the type specific protective determinant of a streptococcal M protein. The complete primary structure of CB6 and CB7 each represent 35 amino acid fragments of a larger polypeptide molecule containing 376 amino acid residues. The present invention found a difference of only 3 of the 35 amino acid residues between CB6 and CB7. Previous studies had shown that the pep M24 molecule is composed of repeating covalent structures and that a type specific antiopsonic determinant is present in each of the repeating structures.

The present study found that antibodies raised against the CB6 or CB7 fragment of pep M24 are opsonic, bactericidal and protective, indicating that the whole pep M24 is not needed for protective immunogenicity. Data indicate, however, that the protective determinant(s) in CB6 and CB7 must be haptenic since the unconjugated peptides lacked immunogenicity. Only when covalently linked with a carrier such as polylysine did the peptides become highly immunogenic in laboratory animals. It was noted that the opsonic antibodies raised against CB7 could be completely absorbed by CB6, CB7 and pep M24 but could be absorbed less well with CB1 and CB2. The finding was important because CB1 and CB2 were shown previously to be considerably more efficient than CB6 and CB7 in absorbing opsonic antibodies prepared in rabbits against uncleaved pep M24.

Although the multiplicity of the antigenic determinants of streptococcal M proteins has been pointed out in previous reports, most studies focusing on distinct precipitating and opsonic antigenic determinants, the present data provide definitive evidence that the pep M24 molecule contains at least 2 distinct opsonic antigenic determinants, each of which is capable of raising type specific protective antibodies against group A streptococci.

EXAMPLE 1

The complete amino acid sequence of two cyanogen bromide peptide fragments (CB6 and CB7) of type 24 streptococcal M protein purified from a peptic extract of the organism was determined by automated Edman degradation of the uncleaved peptides and their tryptic peptides. The sequence of CB6 was found to be Asn-Phe-Ser-Thr-Ala-Asp-Ser-Ala-Lys-Ile-Lys-Thr-Leu-Glu-Ala-Glu-Lys-Ala-Ala-Leu-Glu-Ala-Arg-Gln-Ala-Glu-Leu-Glu-Lys-Ala-Leu-Glu-Gly-Ala-Hse. The sequence of CB7 was identical except for substitutions of Ala, Lys and Asp at positions 21, 24 and 26, respectively. The protective immunogenic properties of these peptide fragments were studied in rabbits. Although neither peptide was immunogenic alone, when covalently conjugated with a polylysine carrier both became highly immunogenic, producing type specific opsonic and bactericidal antibody responses against the type 24 vaccine strain of *Streptococcus pyogenes*. Agar gel diffusion studies indicated the presence of a precipitating antigenic determinant which was shared by the uncleaved pep M24 and the two larger cyanogen bromide peptides, CB1 and CB2. Cross-absorption studies of the opsonic antisera indicated that, although CB6 and CB7 shared antiopsonic determinants with each other and with CB1 and CB2, each of the peptides contained additional antiopsonic determinants which were clearly distinct from the shared determinants. The studies provide the most definitive evidence that the M protein possesses several distinct antiopsonic determinants of known primary structure which are capable of inducing the formation of type-specific opsonic, and presumably protective, antibodies against *S. pyogenes* infections.

Because the opsonic (or protective) determinant appeared to reside in each of the repeating structures, two of the fragments, CB6 and CB7, were selected for detailed chemical and immunochemical analyses. When covalently coupled with a polylysine carrier, both peptides became highly immunogenic, producing type specific opsonic antibodies against streptococci in rabbits. Immunoabsorption studies showed, however, that the opsonic antibodies raised against the peptide fragments, although type specific, were directed at determinants in addition to those raised against the uncleaved pep M24 protein. These studies raise the possibility that each M protein possesses a number of distinct, type-specific protective determinants and that antibodies directed against one or more of these determinants are able to opsonize *S. pyogenes* organisms of the homologous serotype. Furthermore, they indicate that the chemically defined protective determinants of M protein may be separated from potentially harmful regions of the molecule.

EXAMPLE 2

Materials and Methods

Purification of Streptococcal M Protein: M protein was prepared from limited peptic digests of type 24, group A streptococci as described in Beachey et al, *J. Exp. Med.*, 145:1469–1483, (1977) and Beachey et al, *Proc. Natl. Acad. Sci. USA,* 75:3163–3167 (1978). The purified product, hereafter called pep M24, was judged to be pure by SDS-gel electrophoresis and amino acid analysis.

Cleavage with Cyanogen Bromide (CNBr): Fifty-milligram samples of purified pep M24 were dissolved in 20 ml of 70% formic acid and digested under $N_2$ with CNBr at 40° C. for 4 hrs. The digests were diluted with 10 vol of ice-cold distilled water and lyophilized. The CNBr peptides were separated and purified by gel filtration through a column of Sephadex G50 SF (Pharmacia Fine Chemicals, Inc., Piscataway, N.J.) followed by ion exchange chromatography at 43° C. on columns of carboxymethyl-cellulose (Whatman CM52).

Enzymatic Hydrolysis: Digestions with trypsin (TPCK-treated, 3×crystallized, Worthington) were performed in 0.05 M $NH_4HCO_3$, pH 8.3. An enzyme to substrate ratio of 1:50 (w/w) was used as described in Seyer et al, *Biochemistry,* 16:1158–1164 (1977). In some experiments intact pep M24 was maleylated prior to trypsin digestion to limit the cleavage to Arg residues. Recrystallized maleic anhydride was used (20-fold molar excess over the total number of lysyl residues) and demaleylation was achieved with pyridine:acetate (1:10), pH 3.0 at 60° C. for 6 hours.

Separation of Tryptic Peptides of CB6, CB7 and Maleylated Pep M24: Tryptic peptides of CB6 and CB7 were separated by automated peptide analysis on a 0.9×24 cm column of PA-35 resin (Beckman Instruments, Palo Alto, Calif.) at 60° C. Separation was achieved by utilizing a nin-chamber gradient mixer starting with 0.02 M sodium citrate buffer, pH 3.8 (Technician, Peptide Methodology) and an automatic peptide analyzer (Technician Instruments, Inc., Ardsley, N.Y.) equipped with a stream-splitting device which allowed continuous monitoring of ninhydrin reactive peptides on 10% of the column effluent while collecting fractions of the remaining 90% of the effluent. The pH of each of the pooled fractions was adjusted to 2.0 with 1NHCl and desalted on 1×2 cm columns of Aminex 50×8 (200–400 mesh, Bio-Rad Laboratories, Richmond, Calif.).

The peptides obtained after maleylation, trypsin digestion and demaleylation of pep M24 were initially separated according to size by Sephadex G50S gel filtration using a 3.0×110 cm column equilibrated with 0.1 M acetic acid. The UV absorbing peaks were collected, lyophilized and further separated by ion exchange chromatography on 1×20 cm columns of phosphocellulose equilibrated with 0.001 M sodium acetate (pH 3.8) at 43° C. The adsorbed peptides were eluted with a linear gradient from 0 to 0.6 M NaCl over a total volume of 1000 ml. Fractions were pooled, lyophilized, redissolved in 0.1 M acetic acid, desalted on columns of Sephadex G25 in 0.1 M acetic acid, and then re-lyophilized.

Analytic Methods: Amino acid analyses were performed as described in Kang, *Biochemistry,* 11:1828–1835 (1972). Samples were hydrolyzed in doubly distilled, constant boiling HCl under an atmosphere of nitrogen for 24 hrs at 108° C. The hydrolyzed samples were then analyzed on a Beckman 121 automatic amino acid analyzer (Beckman Instruments, Inc., Palo Alto, Calif.) by a single column technique with a four-buffer elution system. No corrections were made for the loss of labile amino acids (threonine, serine, methionine, and tyrosine) or the incomplete release of valine.

Automated Edman degradations were performed with a Beckman Sequencer (model 890C, Beckman Instruments, Inc., Fullerton, Calif.) according to the principles first described by Edman and Begg in *Eur. J. Biochem.,* 1:80–91 (1967). The slow peptide-DMAA (071472) program of Beckman Instruments was used. The phenylthiohydantoin-amino acids were identified by high-pressure liquid chromatography. Arginine derivatives were identified as their parent amino acids after hydrolysis with 55% HI. Repetitive yields of 97% were obtained during automated Edman degradation.

EXAMPLE 3

Conjugation of CB6 and CB7 with Polylysine

CB6 and CB7 were conjugated to polylysine with carbodiimide. The conjugation mixtures consisted of 15 nmol of polylysine (M.W.-35,000, Sigma Chemical Co., St. Louis, Mo.), 75 nmol CB6 or CB7 and 3 mg cyanamide (Carbodiimide; hydrogen cyanomide, Sigma Chemical Co., St. Louis, Mo.) mixed in a total volume of 1.575 ml distilled water. The mixtures were stirred for 18 hrs at 22° C., dialyzed for 24 hrs against distilled water and for 6 hrs against 0.15 M NaCl and then stored frozen at −70° C.

In the above it was found that the reaction was carried out optimally at room temperature. Additionally, for the three reactants the amount of cyanamide is in significant excess to that of the polylysine and the CB6 and CB7.

EXAMPLE 4

Rabbit Immunization

To test the immunogenicity of CB6 and CB7, New Zealand White rabbits (2 Kg) were injected subcutaneously with 25 nmol doses of unconjugated or polylysine-conjugated peptides emulsified in complete Freund's adjuvant. Rabbits were bled immediately before the immunizing injection and at two-week intervals thereafter. In some cases, rabbits were given booster intraperitoneal (2.5 nmol) and intravenous (25 nmol)

injections of CB7 dissolved in 0.15 M NaCl on consecutive days, and sera were then collected 7–14 days after the intravenous injection. To prepare antisera against the intact pep M24 molecule, rabbits were similarly immunized with 3 nmol of uncleaved pep M24. All sera were stored at 4° C.

Immunogenicity of CB6 and CB7

Previous studies in Beachey et al, *Streptococcal Diseases and the Immune Response*, eds. Zabriskie et al, Academic Press, New York, 1979, and Beachey et al, *Proc. Natl. Acad. Sci. USA*, 75:3163–3167 (1978) had shown that each of the 7 CNBr fragments of type 24 M protein was capable of inhibiting type specific opsonic antibodies for type 24 streptococci. It was of interest, therefore, to determine whether or not the 35-amino-acid-segments whose complete sequences are described above were capable of eliciting a type specific immune response in rabbits. In the initial studies, none of 3 rabbits produced opsonic antibodies after immunization with 25 nmol of CB7 emulsified in complete Freund's adjuvant and injected subcutaneously into rabbits.

Assays for opsonic antibodies at 2-week intervals indicated a type specific immune response in 2 of the 3 rabbits immunized with polylysine-conjugated CB6 and in 2 of the 3 rabbits immunized with polylysine conjugated CB7. Bactericidal tests confirmed the protective effect of these opsonic antisera (see Table I).

Immunodiffusion tests in agar gels of the anti-CB7 (conjugated) sera indicated that the antisera reacted with the intact pep M24 molecule as well as with CB1 and CB2 in a precipitin line of identity with the polylysine conjugated CB7. The absence of a precipitin line with the unconjugated CB7 supported the haptenic nature of the peptide fragment. Similar results were obtained with anti-CB6 and polylysine CB6. These results indicated that the CB6 and CB7 fragments of type 24 M protein contained both type-specific opsonic and type-specific precipitating antigenic determinant(s).

Inhibition of Anti-CB7-Induced Opsonization by CNBr Peptides

Opsonic antibodies raised in rabbits against the intact M protein molecule can be inhibited by each of the 7 purified cyanogen bromide peptides of type 24 M protein. Inhibition studies of the rabbit antiserum against CB7, however, showed that while CB7, CB6 and the intact M protein molecule were effective inhibitors of opsonization, CB1 was less effective and CB2 was without effect (all tested at identical doses of 5 nmol) (see Table II). In another experiment using antisera prepared against CB7, CB1 and the uncleaved pep M24, it was found that, whereas eight times more CB7 than CB1 was needed to inhibit the opsonic effect of anti-pep M24, thirteen times more CB1 than CB7 was needed to inhibit the opsonic effect of anti-CB7. Conversely, 33 times more CB7 than CB1 was needed to inhibit the opsonic effect of anti-CB1 (see Table III). These results suggested that the M protein molecule must contain more than one type specific opsonogenic determinant and further supported the heterogeneity of the type specific antigenic determinants of the M protein molecule.

TABLE I

Indirect Bactericidal Tests of Sera of Rabbits Immunized With CB7-Polylysine Conjugate

| Rabbit Serum Collected at 2-Week Intervals After Immunization With CB7[a] | No. of Colonies of Type 24 Streptococci After 3 h Growth in Test Mixtures[b] | |
|---|---|---|
| | 34 | 6 |
| Pre-immune | 2000 | 422 |
| 4 wk | 567 | 56 |
| 6 wk | 56 | 3 |
| 8 wk | 134 | 0 |
| 10 wk[c] | 81 | 7 |
| 13 wk[c] | 35 | 6 |
| 16 wk | 15 | 0 |

[a]Rabbits were immunized with 25 nmol of CB7-polylysine emulsified in complete Freund's adjuvant in a total volume of 1 ml which was injected into multiple intracutaneous sites behind the neck. The results recorded in Table I were obtained with a pool of the sera from the 2 rabbits showing an immune response in phagocytosis tests. Similar results were obtained with the sera of the rabbits immunized with CB6-polylysine (results not shown in Table).
[b]Test mixtures consisted of 0.4 ml heparinized (10 U/ml) fresh human blood, 0.05 ml rabbit serum, and an inoculum of 0.05 ml of a suspension of streptococci containing the number of colony forming units indicated. The mixtures were incubated end-over-end for 3 hrs after which pour plates were prepared from the mixtures and 20 ml of 5% sheep blood agar.
[c]Intravenous booster doses of 25 nmol of CB7-polylysine given at 9 and 12 weeks.

TABLE II

Absorption of Opsonic Antibodies from Anti-CB7 Rabbit Serum with Pep M24 Cyanogen Bromide Fragments

| Antisera Absorbed[a] with: | % Phagocytosis in Antiserum Against: | |
|---|---|---|
| | CB7 | Pep M24 |
| Unabsorbed | 72 | 78 |
| CB7 | 2 | 3 |
| CB6 | 11 | 2 |
| CB1 | 50 | 4 |
| CB2 | 80 | 6 |
| Uncleaved pep M24 | 4 | 2 |
| Heterologous pep M6 | 70 | 74 |

[a]0.1 ml of diluted antiserum absorbed with 5 nmol of the respective antigens dissolved in 0.1 ml NaCl/P$_i$ before using the sera to opsonize type 24 streptococci as described in Example 2.

TABLE III

Cross-absorption of Type 24 Opsonic Antibodies From Rabbit Antisera Prepared Against CB7, CB1 and the Uncleaved Pep M24

| Rabbit Antiserum | Minimal dose (nmol) required to absorb opsonic antibodies[a] with | | |
|---|---|---|---|
| | CB7 | CB1 | pep M24 |
| Anti-CB7 | 0.65 | 8.5 | 0.05 |
| Anti-CB1 | 6.5 | 0.2 | 0.02 |
| Anti-pep M24 | 1.6 | 0.2 | 0.05 |

[a]0.1 ml of the highest dilution of opsonic antiserum able to promote phagocytosis in 40–60% of neutrophilic leukocytes in phagocytosis assays was absorbed with 0.1 ml of the respective antigens. The absorbed serum was then used to preopsonize type 24 streptococci as described in Example 2.

I claim:
1. The conjugation of M24 protein particle CB6 or CB7 with polylysine which produces a conjugation antisera against animal streptococcus infection.
2. The conjugation according to claim 1 wherein CB6 is utilized as an immunogenic agent.
3. The conjugation according to claim 1 wherein CB7 is utilized as an immunogenic agent.
4. A process of producing a conjugate of CB6 or CB7 or both with polylysine.
5. The process according to claim 4 wherein additionally the reactants were subjected to a dialysis for an extended period of time.
6. The process according to claim 5 wherein the reactants were stirred for 18 hours.

* * * * *